United States Patent
Li et al.

(10) Patent No.: US 9,604,941 B2
(45) Date of Patent: Mar. 28, 2017

(54) PREPARATION METHOD OF CONJUGATED COMPOUND CONTAINING BIS(PHENYLSULFONYL)BENZENE STRUCTURE AND AN ORGANIC ELECTROLUMINESCENT DIODE DEVICE USING THE CONJUGATED COMPOUND

(71) Applicant: Shenzhen China Star Optoelectronics Technology Co., Ltd., Shenzhen (CN)

(72) Inventors: Xianjie Li, Shenzhen (CN); Yuanchun Wu, Shenzhen (CN); Shijian Su, Shenzhen (CN); Kunkun Liu, Shenzhen (CN); Ming Liu, Shenzhen (CN)

(73) Assignee: SHENZHEN CHINA STAR OPTOELECTRONICS TECHNOLOGY CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 14/763,830

(22) PCT Filed: May 22, 2015

(86) PCT No.: PCT/CN2015/079539
§ 371 (c)(1),
(2) Date: Jul. 28, 2015

(87) PCT Pub. No.: WO2016/173020
PCT Pub. Date: Nov. 3, 2016

(65) Prior Publication Data
US 2016/0322567 A1    Nov. 3, 2016

(30) Foreign Application Priority Data
Apr. 28, 2015 (CN) .......................... 2015 1 0207961

(51) Int. Cl.
*H01L 21/00* (2006.01)
*C07D 241/46* (2006.01)
(Continued)

(52) U.S. Cl.
CPC .......... *C07D 241/46* (2013.01); *C07C 315/04* (2013.01); *C07C 317/14* (2013.01);
(Continued)

(58) Field of Classification Search
CPC ..... H01L 51/00; C07C 315/04; C07C 317/14; C07C 317/36; C07D 213/34;
(Continued)

(56) References Cited

U.S. PATENT DOCUMENTS

2004/0023062 A1* 2/2004 Kathirgamanathan . C09K 11/06
428/690
2011/0190409 A1* 8/2011 Du ........................ B01D 53/02
521/119

(Continued)

FOREIGN PATENT DOCUMENTS

CN       1829702 A    9/2006
CN     102186813 A    9/2011

*Primary Examiner* — Caleb Henry
(74) *Attorney, Agent, or Firm* — Leong C. Lei

(57) ABSTRACT

The invention provides a conjugated compound containing a bis(phenylsulfonyl)benzene structure, a preparation method and an application thereof, the compound includes a chemical structure with one of structural general formulas as follows:

formula A (Continued)

-continued

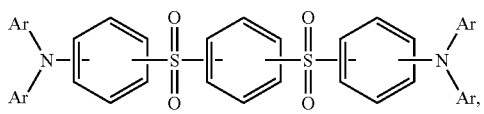

formula B the invention obtains a conjugated compound containing a bis(phenylsulfonyl)benzene structure by selecting multiple kinds of conjugated aromatic units to react with halogen-substituted bis(phenylsulfonyl)benzene in the manner of Suzuki coupling reaction, Buchwald-Hartwig coupling reaction or copper-catalyzed halogenated aromatic amination reaction. The novel compound prepared by the invention has the characteristic of fluorescence as well as a certain electrical conductivity, and thus can be applied to fabricate a light-emitting layer or an electron transport layer of an organic electroluminescent diode.

10 Claims, 3 Drawing Sheets

(51) Int. Cl.
| | | |
|---|---|---|
| C09K 11/06 | (2006.01) |
| C07C 315/04 | (2006.01) |
| C07C 317/14 | (2006.01) |
| C07D 213/34 | (2006.01) |
| H01L 51/00 | (2006.01) |
| C07D 209/86 | (2006.01) |
| C07C 317/36 | (2006.01) |
| C07D 219/02 | (2006.01) |
| C07D 265/38 | (2006.01) |
| C07D 279/22 | (2006.01) |
| H01L 51/50 | (2006.01) |

(52) U.S. Cl.
CPC .......... *C07C 317/36* (2013.01); *C07D 209/86* (2013.01); *C07D 213/34* (2013.01); *C07D 219/02* (2013.01); *C07D 265/38* (2013.01); *C07D 279/22* (2013.01); *C09K 11/06* (2013.01); *H01L 51/0059* (2013.01); *H01L 51/0067* (2013.01); *H01L 51/0071* (2013.01); *H01L 51/0072* (2013.01); *C09K 2211/1007* (2013.01); *C09K 2211/1014* (2013.01); *C09K 2211/1022* (2013.01); *C09K 2211/1029* (2013.01); *C09K 2211/1033* (2013.01); *C09K 2211/1037* (2013.01); *C09K 2211/1044* (2013.01); *H01L 51/5012* (2013.01)

(58) Field of Classification Search
CPC .. C07D 241/46; C07D 219/02; C07D 265/38; C07D 279/22; C07D 209/86; C09K 11/06
See application file for complete search history.

(56) References Cited

U.S. PATENT DOCUMENTS

2014/0061545 A1* 3/2014 Leroy ............... C09K 11/06
 252/500
2015/0137083 A1* 5/2015 Cheng ............. H01L 51/0059
 257/40

* cited by examiner

PREPARATION METHOD OF CONJUGATED COMPOUND CONTAINING BIS(PHENYLSULFONYL)BENZENE STRUCTURE AND AN ORGANIC ELECTROLUMINESCENT DIODE DEVICE USING THE CONJUGATED COMPOUND

TECHNICAL FIELD

The invention relates to the field of electroluminescent material, and particularly to a conjugated compound containing bis(phenylsulfonyl)benzene structure, a preparation method and an application thereof.

DESCRIPTION OF RELATED ART

In recent twenty years, owing to its advantages such as high efficient, low-voltage drive, easy to be prepared for a large area and full-color display, the organic light emitting diode (OLED) has got a wide application prospect and thus got people's attention. A research has begun in the 50s of the last century, and until 1987, Dr. Deng Qingyun, etc. of Kodak has proposed a sandwich device structure in the patent No. U.S. Pat. No. 4,356,429 and the developed OLED device has an emission brightness being up to 1000 cd/m$^2$ when being driven at 10V direct current voltage, so that the OLED has gained a landmark development.

The organic electroluminescent is divided into fluorescence and phosphorescence, according to a spin quantum statistical theory, a probability of singlet state exciton to triplet state exciton is 1:3, that is, a theoretical limit of fluorscence resulting from a radiative transition of singlet state exciton is 25%, and a theoretical limit of phosphorescence resulting from a radiative transition of triplet state exciton is 75%. Owing to a spin-forbidden, in a conventional pure organic molecule compound, the triplet state excitons cannot directly emit light by radiative transition and only can decay to the ground state in the form of heat radiation, which results in the waste of most excitons and energy loss. How to make use of the 75% energy of triplet exciton has become an urgent priority. In the year of 2012, Adachi has discovered a class of compounds containing a sulfonyl group which have a smaller singlet-triplet energy gap, so that the excitons in the triplet state can jump to the singlet state through an anti-interstitial and then can emit fluoresce by radiative transition, so that the theoretical limit of all fluorescence is much more than 25%. Devices prepared by doping such compound containing the sulfonyl group as a light-emitting unit in a host material of bis(2-(diphenylphosphoryl oxy)phenyl)ether (DPEPO) can achieve an external quantum efficiency up to 9.9%, and thus is much higher than the level achieved by the traditional organic fluorescent compounds. Since then, people get a strong interest in the electroluminescent compounds with the smaller singlet-triplet energy gap, and in which, the compound containing the sulfonyl group plays a very important role.

In order to achieve the smaller singlet-triplet energy gap, there is a strict requirement on the design for materials, such as the controls to a conjugate length as well as an interaction between electron donors and electron acceptors. So far, a very small number of materials can achieve the transition of triplet state excitons reversely jumping to be the single excitons in electroluminescent devices. For the conventional organic light-emitting molecules, the interaction between electron donors and electron acceptors is excessively strong and a conjugation extent of the molecules is too large, which result in a lower energy level of triplet state and thus it is difficult to achieve the smaller singlet-triplet energy gap. Therefore, it is needed to develop a new structural unit to control an intramolecular charge-transfer in a reasonable extent.

SUMMARY

In order to overcome the drawbacks and shortcomings of the prior art, a first objective of the invention is to provide a conjugated compound containing a bis(phenylsulfonyl)benzene structure, which has a high fluorescence quantum yield and is beneficial to improve the light-emitting efficiency of electroluminescent device.

Another objective of the invention is to provide a preparation method of the above-mentioned conjugated compound containing a bis(phenylsulfonyl)benzene structure, which is simple, easy to operate and can achieve a high yield of target product.

A further another objective of the invention is to provide an application of the above-mentioned conjugated compound containing a bis(phenylsulfonyl)benzene structure in an organic light-emitting diode device, by applying the conjugated compound containing a bis(phenylsulfonyl)benzene structure in a light-emitting layer of the organic light-emitting diode device, the light-emitting efficiency of organic light-emitting diode device can be significantly improved.

The objectives of the invention are carried out by the following solutions:

in particular, a conjugated compound containing bis(phenylsulfonyl)benzene structure, includes a chemical structure with one of structural general formulas as follows:

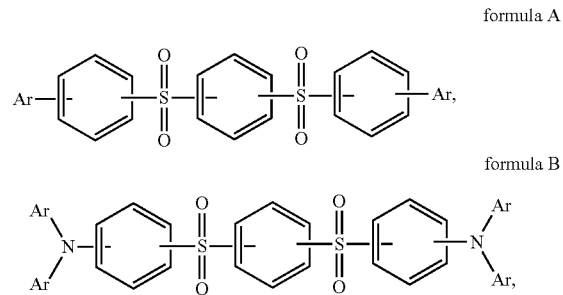

in the formula A and the formula B, each benzene ring being covalently bonded with adjacent sulfonyl group, Ar unit or N(Ar)$_2$ unit at an arbitrary position;

the Ar unit has a conjugated structure and is one of aromatic rings constituted by vinylene group, ethynylene group and hydrogen and carbon atoms, aromatic heterocyclic rings constituted by carbon, nitrogen and hydrogen atoms, aromatic heterocyclic rings constituted by carbon, nitrogen, oxygen and hydrogen atoms, aromatic heterocyclic rings constituted by carbon, sulfur and hydrogen atoms, aromatic heterocyclic rings constituted by carbon, silicon and hydrogen atoms, aromatic heterocyclic rings constituted by carbon, nitrogen, sulfur and hydrogen atoms, aromatic heterocyclic rings constituted by carbon, silicon, sulfur and hydrogen atoms, and any combinations thereof.

In a preferred embodiment, the middle benzene ring is covalently bonded with the adjacent sulfonyl group in the form of meta-position or para-position, the benzene rings at both sides of the sulfonyl group each are covalently bonded with the adjacent Ar unit or N(Ar)2 unit in the form of para-position, and thereby the conjugated compound containing a bis(phenylsulfonyl)benzene structure has a chemical structure with one of structural general formulas as follows:

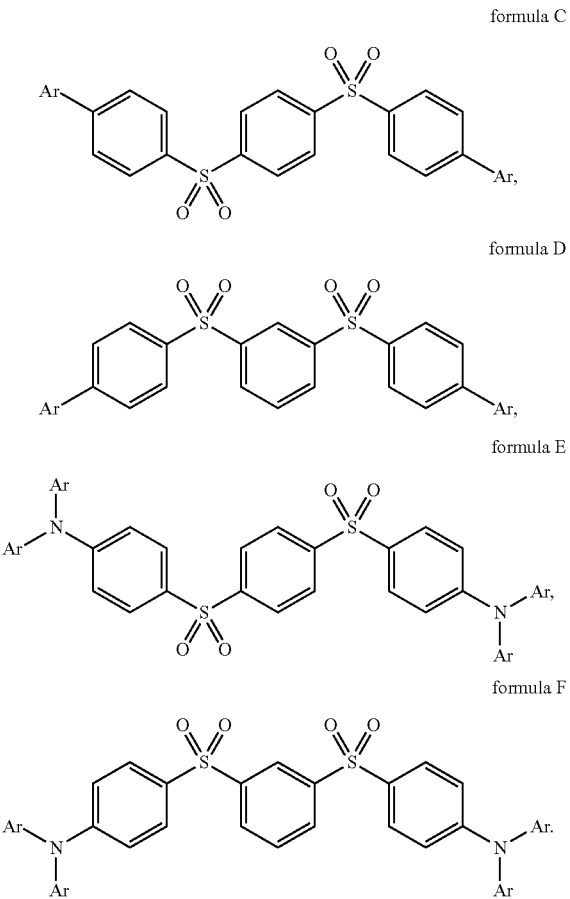

formula C formula D formula E formula F

In particular, a preparation method of the above-mentioned conjugated compound containing a bis(phenylsulfonyl)benzene structure includes following steps:

step 10, synthesizing a precursor of halogen-substituted bis(phenylsulfonyl)benzene;

step 20, making the synthesized precursor of halogen-substituted bis(phenylsulfonyl)benzene to react with a borate ester compound of a Ar unit in the presence of catalyst in a manner of Suzuki coupling reaction, to thereby prepare the conjugated compound containing a bis(phenylsulfonyl)benzene structure, and a reaction equation is as follows:

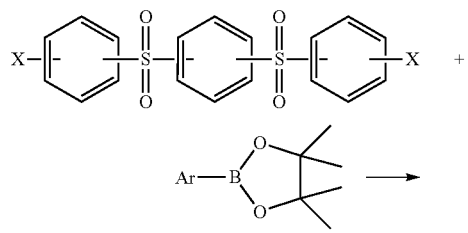

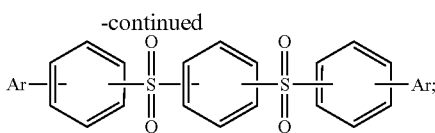

or, step 20', making the synthesized precursor of halogen-substituted bis(phenylsulfonyl)benzene to react with a NH(Ar)$_2$ compound containing secondary amine atoms in a manner of Buchwald-Hartwig coupling reaction (Buchwald-Hartwig reaction) or copper-catalyzed halogenated aromatic amination reaction to thereby prepare the conjugated compound containing a bis(phenylsulfonyl)benzene structure, and a reaction equation is as follows:

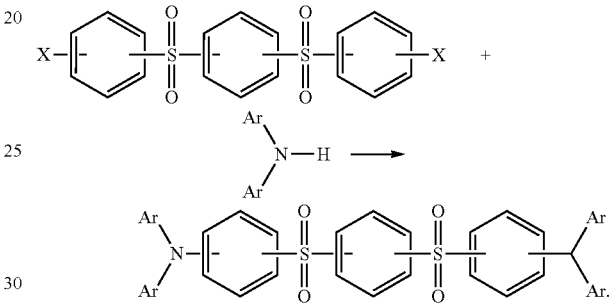

In a preferred embodiment, the step 10 concretely includes following steps:

step 11, dissolving a halogenated thiophenol and a dichloro-dicyano-p-benzoquinone (DDQ) in a solvent, heating to react, and thereby obtaining a halogenated diphenyl disulfide;

step 12, dissolving the halogenated diphenyl disulfide, a dihalogeno-benzene, a catalyst and an alkali in a solvent, heating to react and thereby obtaining a halogen-substituted bis(phenylsulfenyl)benzene;

step 13, dissolving the halogen-substituted bis(phenylsulfenyl)benzene in a solvent, adding an oxidizer, heating to react and thereby obtaining the halogen-substituted bis(phenylsulfonyl)benzene.

In a preferred embodiment, the step 20 concretely is that dissolving the synthesized halogen-substituted bis(phenylsulfonyl)benzene, the borate ester of the Ar unit, the catalyst and the alkali in a solvent, heating to react and thereby obtaining the conjugated compound containing a bis(phenylsulfonyl)benzene structure;

the step 20' concretely is that dissolving the synthesized halogen-substituted bis(phenylsulfonyl)benzene, the NH(Ar)$_2$ compound containing secondary amine atoms, the catalyst and the alkali in a solvent, heating to react and thereby obtaining the conjugated compound containing a bis(phenylsulfonyl)benzene structure.

In a preferred embodiment, in the step 11, a molar ratio of the halogenated thiophenol to the dichloro-dicyano-p-benzoquinone is 2:1;

in the step 12, a molar ratio of the halogenated diphenyl disulfide, the dihalogeno-benzene, the catalyst and the alkali is (1~1.2):1:(0.02~0.05):(2~6);

in the step 13, a molar ratio of the halogen-substituted bis(phenylsulfenyl)benzene to the oxidizer is 1:(5~8);

in the step 20, a molar ratio of the halogen-substituted bis(phenylsulfonyl)benzene, the borate ester of the Ar unit, the catalyst and the alkali is 1:(2.2~3):(0.02~0.05):(3~6);

in the step 20', a molar ratio of the halogen-substituted bis (phenylsulfonyl) benzene, the NH(Ar)2 compound containing secondary amine atoms, the catalyst and the alkali is 1:(2.2~3):(0.05~0.1):(3~6).

In a preferred embodiment, in the step 11, the halogenated thiophenol is at least one kind of ortho-bromobenzenethiol, para-bromobenzenethiol and meta-bromobenzenethiol;

in the step 12, the dihalogeno-benzene is at least one of para-diiodobiphenyl and meta-diiodobiphenyl, the catalyst is at least one kind of cuprous sulfide, cuprous iodide and cuprous oxide;

in the step 13, the oxidizer is at least one of hydrogen peroxide, potassium permanganate and pyridinium chlorochromate;

in the step 20, the catalyst is at least one of tetrakis (triphenylphosphine)palladium, tetrakis(triphenylphosphine)palladium dichloride, tris(dibenzylideneacetone) dipalladium and phosphorus tricyclohexylphosphine;

in the step 20', the catalyst is one of palladium acetate, tri-butyl phosphine and 1,1'-bis (diphenylphosphino) ferrocene;

in the steps 12, 20 and 20', the alkalis are at least one of potassium carbonate, sodium carbonate and potassium phosphate;

in the steps 11, 12, 13, 20 and 20', the solvents are at least one of toluene, ethanol, 1,4-dioxane, tetrahydrofuran, dimethyl sulfoxide, methylene chloride, N, N-dimethylformamide and 1,3-dimethyl-3,4,5,6-tetrahydro-2-pyrimidone.

In particular, an organic electroluminescent diode device, comprising a substrate, an anode, a hole transport layer, an electron blocking layer, a light-emitting layer, a hole blocking layer, an electron transport layer and a cathode sequentially arranged in that order from bottom to top, a material of the light-emitting layer is a host material doped with the above-mentioned conjugated compound containing a bis (phenylsulfonyl)benzene structure, the host material is bis (o-phenylene diphenyl phosphorus oxy)ether.

In a preferred embodiment, the substrate is a glass substrate, a material of the anode is indium tin oxide, the cathode is a double-layer composite structure which is composed by a lithium fluoride layer and an aluminum layer.

In a preferred embodiment, a material of the hole transport layer is N,N'-diphenyl-N,N'-(1-naphthyl)-1,1'-biphenyl-4,4'-diamine, a material of the electron blocking layer is 4,4',4"-tris(9-carbazolyl)triphenylamine, a material of the hole blocking layer is 9-4-tert-butylphenyl-3,6-di-triphenylsilyl-9H-carbazole, a material of the electron transport layer is 1,3,5-tris (1-phenyl-1-H-benzimidazol-2-pyrimidone) benzene.

Principles of the invention are that: in a conjugated compound containing a bis(phenylsulfonyl)benzene structure of the invention, using the bis(phenylsulfonyl) as a nucleus, by making use of an electrophilic characteristic of the sulfonyl group, obtaining a class of molecules with intramolecular charge-transfer; and by making use of the barrier effect of the sulfonyl group on a conjugated system, controlling effective conjugated strength of the whole molecule to make the molecule have a high triplet state energy, thus reducing singlet-triplet energy gap, so that the excitons in the triplet state can jump to the singlet state through an anti-interstitial and then can emit fluoresce by radiative transition, so as to improve the utilization efficiency of the excitons, and ultimately to achieve the objective of improving device performance.

Compared with the prior art, embodiments of the invention have advantages and beneficial effects as follows:

(1) the conjugated compound containing a bis(phenylsulfonyl)benzene structure of the invention uses the bis (phenylsulfonyl) as a nucleus, which is a new synthesized product and is provided with novelty and creativity.

(2) the invention provides a method path of the preparation of the conjugated compound containing a bis (phenylsulfonyl)benzene structure.

(3) the conjugated compound containing a bis(phenylsulfonyl)benzene structure of the invention, by bonding different units to adjust the structures, can realize emitted lights with different wave.

(4) the conjugated compound containing a bis(phenylsulfonyl)benzene structure has a higher fluorescence quantum yield, and is beneficial to realize a high light-emitting efficiency of the device.

(5) the conjugated compound containing a bis(phenylsulfonyl)benzene structure has a smaller singlet-triplet energy gap, which is beneficial to improve an utilization rate of the excitons and can break 5% of the external quantum theoretical efficiency limit of traditional fluorescence materials.

In order to further understand features and technical contents of the invention, please refer to following detailed description and accompanying drawings of the invention. The drawings only are used for reference and description and are not intended to limit the invention.

BRIEF DESCRIPTION OF THE DRAWINGS

In the following, with reference to accompanying drawings, concrete embodiments of the invention will be described in detail to make technical solutions and other beneficial effects of the invention more clear.

In the drawings.

DETAILED DESCRIPTION OF EMBODIMENTS

Figure 1:
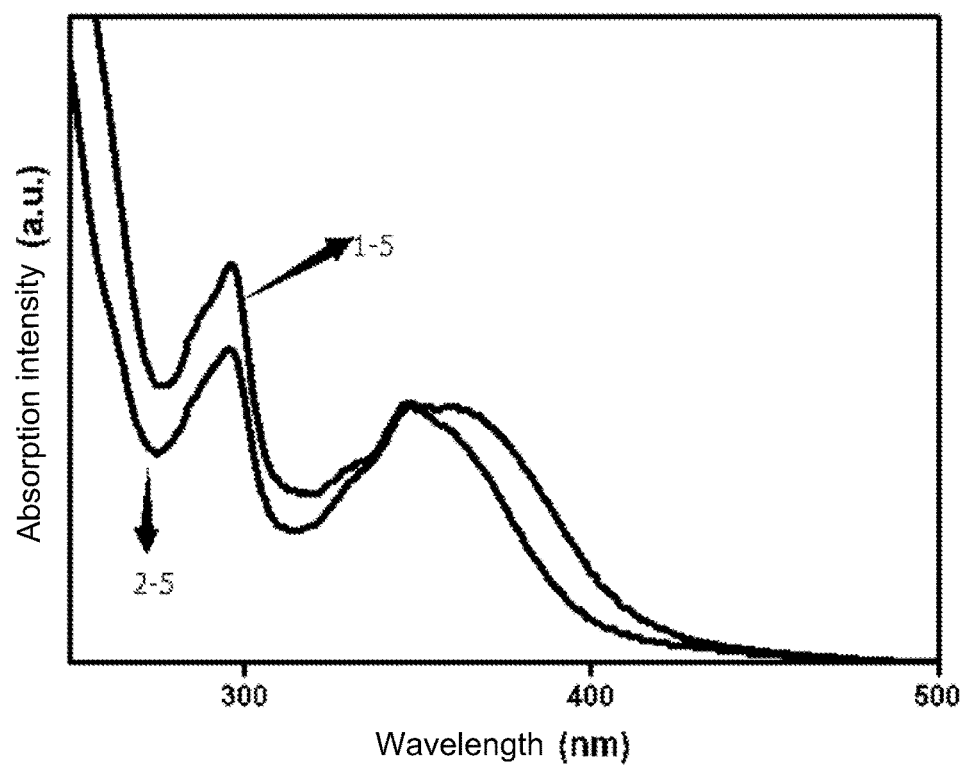
FIG. 1 is an absorption spectra view of ultraviolet-visible light of a solid film of a conjugated compound containing bis(phenylsulfonyl)benzene structure prepared by embodiments 15, 16 of the invention.
Figure 2:
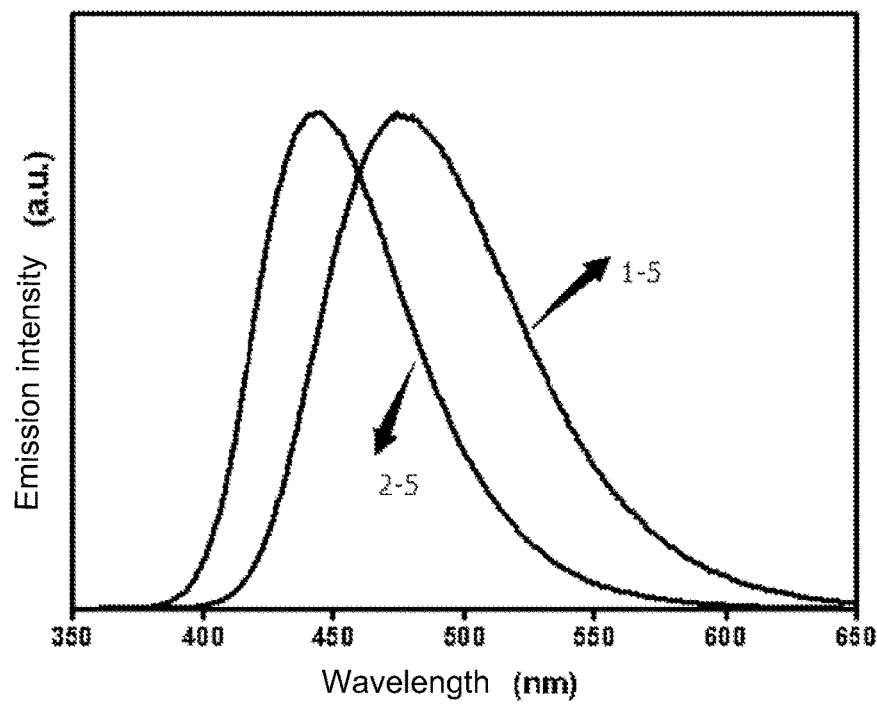
FIG. 2 is a fluorescence spectra view of a solid film of a conjugated compound containing bis(phenylsulfonyl)benzene structure prepared by the embodiments 15, 16 of the invention.

In order to further illustrate technical solutions and effects of the invention, preferred embodiments of the invention with reference to accompanying drawings will be described below in detail.

Embodiment 1:

It is the preparation of a bis(4-bromophenyl)disulfide, and reaction formula is shown as follows:

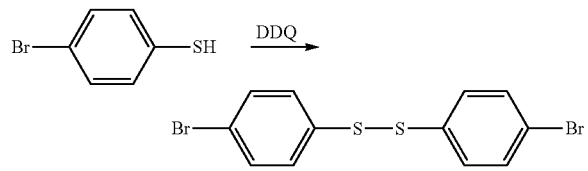

In a 1 L single-necked flask, at the room temperature, adding dichloro-dicyano-p-benzoquinone (DDQ) (0.1 mol, 22.7 g) in 500 ml dichloromethane, then adding 4-bromothiophenol (0.20 mol, 37.8 g), stirring for 1 h. Then pouring the mixed liquor into 1 L water, and extracting a product by dichloromethane. Drying organic phases by anhydrous magnesium sulfate, removing solvent after separating, using silica gel column chromatography for separating and purifying to thereby obtain a yellow solid (34.6 g, the yield is 92%).

Embodiment 2:

It is the preparation of a bis(3-bromophenyl)disulfide, and reaction formula is shown as follows:

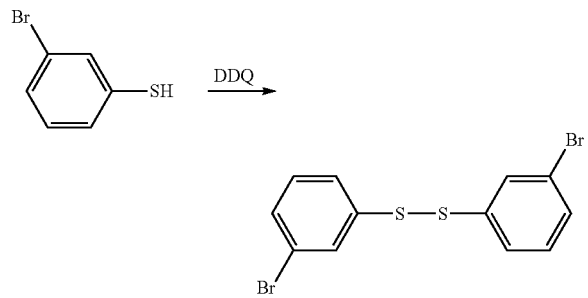

In a 1 L single-necked flask, at the room temperature, adding dichloro-dicyano-p-benzoquinone (DDQ) (0.1 mol, 22.7 g) in 500 ml dichloromethane, then adding m-bromobenzenethiol (0.20 mol, 37.8 g), stirring for 1 h. Then pouring the mixed liquor into 1 L water, and extracting a product by dichloromethane. Drying organic phases by anhydrous magnesium sulfate, removing solvent after separating, using silica gel column chromatography for separating and purifying to thereby obtain a yellow solid (33.4 g, the yield is 89%).

Embodiment 3:

It is the preparation of a 1,4-bis[(4-bromophenyl)sulfur]benzene, and a reaction formula is shown as follows:

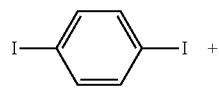

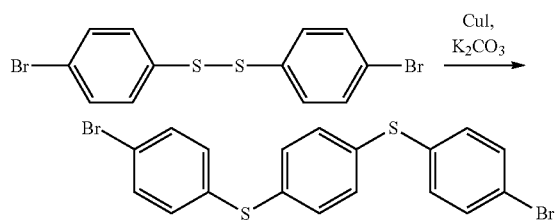

In a 250 ml three-necked flask, at the room temperature, adding bis(4-bromophenyl)disulfide (50 mmol, 18.8 g) and para-diiodobenzene (50 mmol, 16.5 g) to 150 ml dimethyl sulfoxide, then adding cuprous iodide (5 mmol, 1.0 g) and potassium carbonate (150 mmol, 20.7 g). Under an argon atmosphere, heating to 120° C. and reacting for 24 h. Then pouring the mixed liquor into 500 ml water, and extracting a product by dichloromethane. Drying organic phases by anhydrous magnesium sulfate, removing solvent after separating, using silica gel column chromatography for separating and purifying to thereby obtain a white solid (14.5 g, the yield is 64%).

Embodiment 4:

It is the preparation of a 1,3-bis[(4-bromophenyl)sulfur]benzene, and a reaction formula is shown as follows:

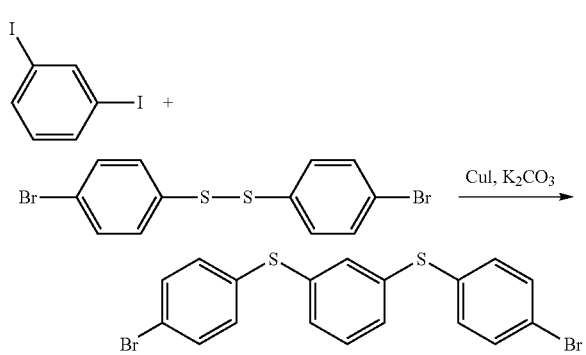

In a 250 ml three-necked flask, adding bis(4-bromophenyl)disulfide (50 mmol, 18.8 g) and m-diiodobenzene (50 mmol, 16.5 g) to 150 ml dimethyl sulfoxide, then adding cuprous iodide (5 mmol, 1.0 g) and potassium carbonate (150 mmol, 20.7 g). Under an argon atmosphere, heating to 120° C. and reacting for 24 h. Then pouring the mixed liquor into 500 ml water, and extracting a product by dichloromethane. Drying organic phases by anhydrous magnesium sulfate, removing solvent after separating, using silica gel column chromatography for separating and purifying to thereby obtain a white solid (13.3 g, the yield is 58%).

Embodiment 5:

It is the preparation of a 1,4-bis[(4-bromophenyl)sulfonyl]benzene, and a reaction formula is shown as follows:

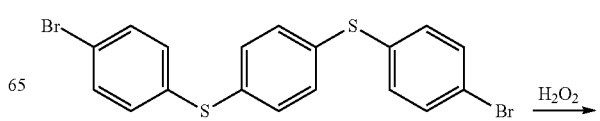

-continued

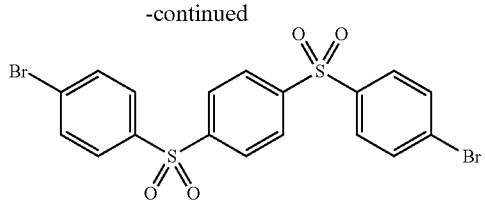

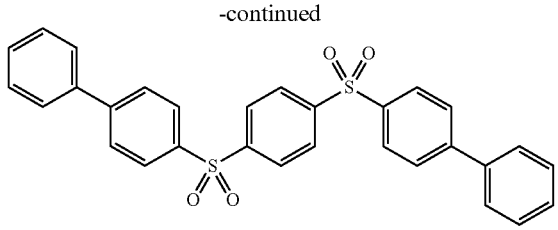

In a 500 ml three-necked flask, adding 1,4-bis[(4-bromophenyl)sulfur]benzene (30 ml, 13.5 g) to 200 ml acetic acid. After heating to 100° C., adding hydrogen peroxide aqueous solution (180 ml, about 19 ml) with a mass concentration of 30%, after stirring for 18 h, pouring the mixed liquor into 500 ml water, and extracting a product by dichloromethane. Drying organic phases by anhydrous magnesium sulfate, removing solvent after separating, using silica gel column chromatography for separating and purifying to thereby obtain a white solid (14.5 g, the yield is 94%).

Embodiment 6:

It is the preparation of a 1,3-bis[(4-bromophenyl)sulfonyl]benzene, and a reaction formula is shown as follows:

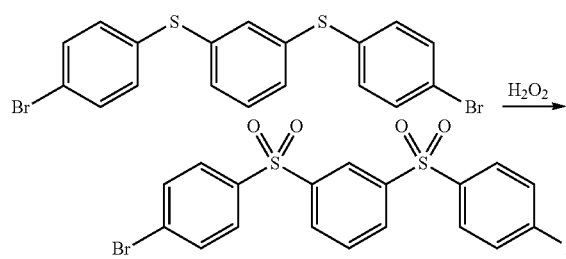

In a 500 ml three-necked flask, adding 1,3-bis[(4-bromophenyl)sulfur]benzene (30 ml, 13.5 g) to 200 ml acetic acid. After heating to 100° C., adding hydrogen peroxide aqueous solution (180 ml, about 19 ml) with a mass concentration of 30%, after stirring for 18 h, pouring the mixed liquor into 500 ml water, and extracting a product by dichloromethane. Drying organic phases by anhydrous magnesium sulfate, removing solvent after separating, using silica gel column chromatography for separating and purifying to thereby obtain a white solid (13.8 g, the yield is 89%).

Embodiment 7:

It is the preparation of a conjugated compound 1-1 containing a bis(phenylsulfonyl)benzene structure, and a reaction formula is shown as follows:

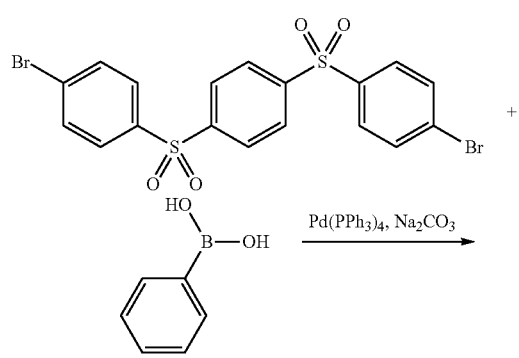

Under an argon atmosphere, adding 1,4-bis[(4-bromophenyl)sulfonyl] benzene (5 mmol, 2.6 g), phenylboronic acid (12 mmol, 1.5 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (1.8 g, the yield is 72%) is obtained.

Embodiment 8:

It is the preparation of a conjugated compound 2-1 containing a bis(phenylsulfonyl)benzene structure, and a reaction formula is shown as follows:

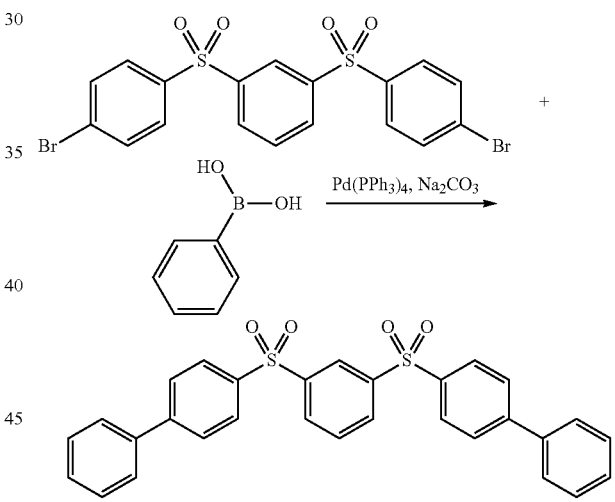

Under an argon atmosphere, adding 1,3-bis[(4-bromophenyl) sulfonyl]benzene (5 mmol, 2.6 g), phenylboronic acid (12 mmol, 1.5 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (1.7 g, the yield is 67%) is obtained.

Embodiment 9:

It is the preparation of a conjugated compound 1-2 containing a bis(phenylsulfonyl)benzene structure, and a reaction formula is shown as follows:

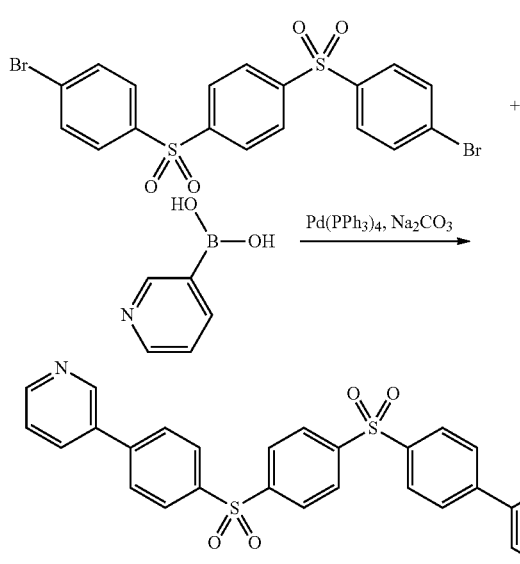

Under an argon atmosphere, adding 1,4-bis[(4-bromophenyl)sulfonyl] benzene (5 mmol, 2.6 g), 3-pyridine boronic acid (12 mmol, 1.5 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (1.7 g, the yield is 68%) is obtained.

Embodiment 10:

It is the preparation of a conjugated compound 2-2 containing a bis(phenylsulfonyl)benzene structure, and a reaction formula is shown as follows:

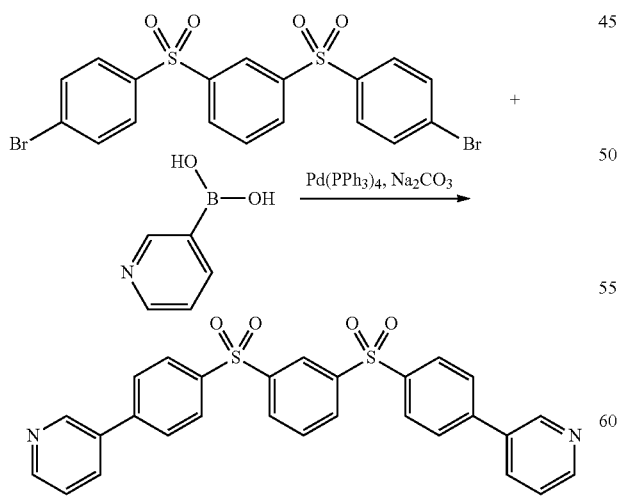

Under an argon atmosphere, adding 1,3-bis[(4-bromophenyl)sulfonyl] benzene (5 mmol, 2.6 g), 3-pyridine boronic acid (12 mmol, 1.5 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (1.6 g, the yield is 62%) is obtained.

Embodiment 11:

It is the preparation of a conjugated compound 1-3 containing a bis(phenylsulfonyl)benzene structure, and a reaction formula is shown as follows:

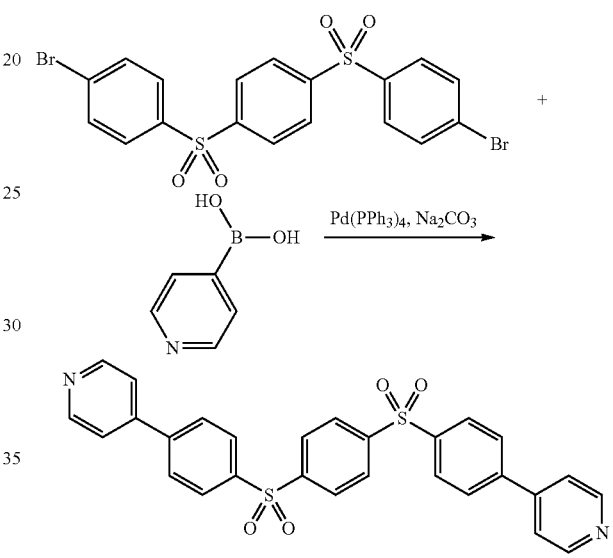

Under an argon atmosphere, adding 1,4-bis[(4-bromophenyl) sulfonyl]benzene (5 mmol, 2.6 g), 4-pyridine boronic acid (12 mmol, 1.5 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid by, and after drying and then vacuum sublimation, a high purity product (1.9 g, the yield is 74%) is obtained.

Embodiment 12:

It is the preparation of a conjugated compound 2-3 containing bis(phenylsulfonyl)benzene structure, and a reaction formula is shown as follows:

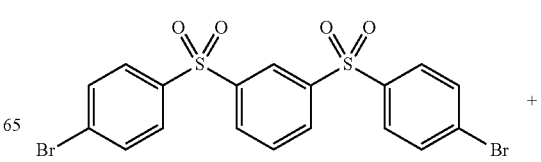

-continued

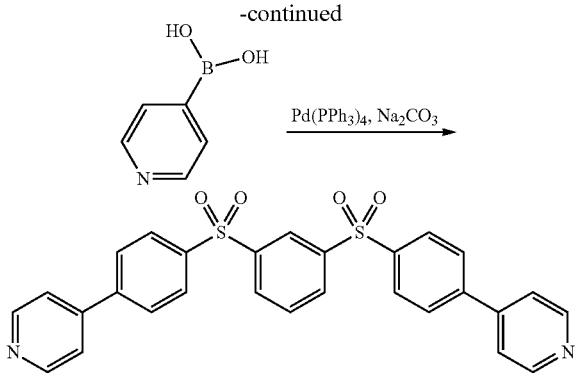

Under an argon atmosphere, adding 1,3-bis[(4-bromophenyl) sulfonyl]benzene (5 mmol, 2.6 g), 4-pyridine boronic acid (12 mmol, 1.5 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (1.8 g, the yield is 71%) is obtained.

Embodiment 13:

It is the preparation of a conjugated compound 1-4 containing a bis(phenylsulfonyl)benzene structure, and a reaction formula is shown as follows:

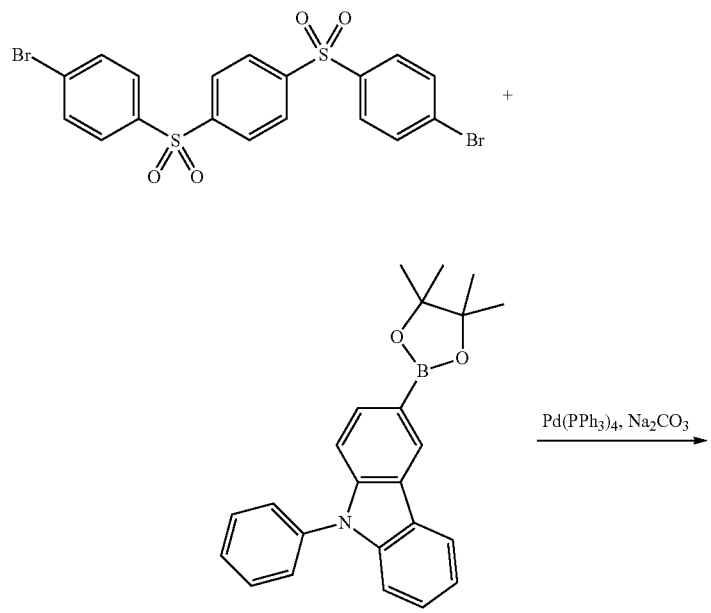

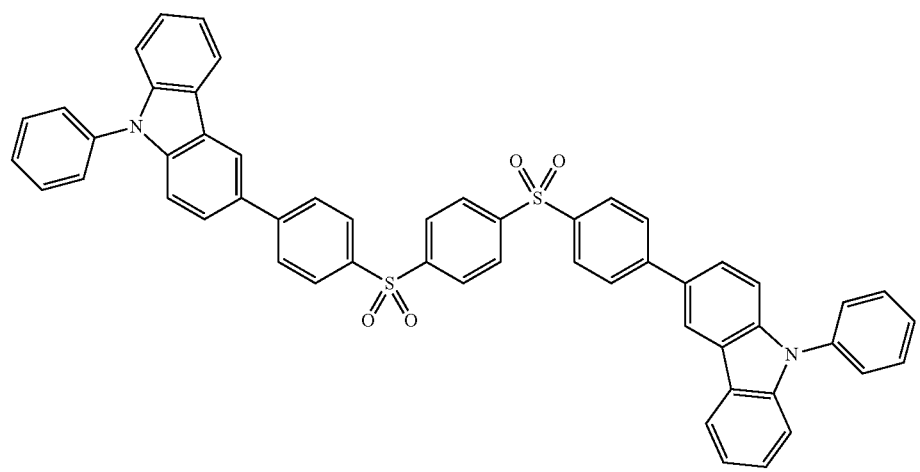

Under an argon atmosphere, adding 1,4-bis[(4-bromophenyl) sulfonyl]benzene (5 mmol, 2.6 g), 9-phenyl-3-(4,4,5,5-tetramethyl-1,3,2-dioxa pentaborane-2-yl)carbazole (12 mmol, 4.4 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and vacuum sublimation, a high purity product (2.5 g, the yield is 59%) is obtained.

Embodiment 14:

It is the preparation of a conjugated compound 2-4 containing a bis(phenylsulfonyl)benzene structure, and a reaction formula is shown as follows:

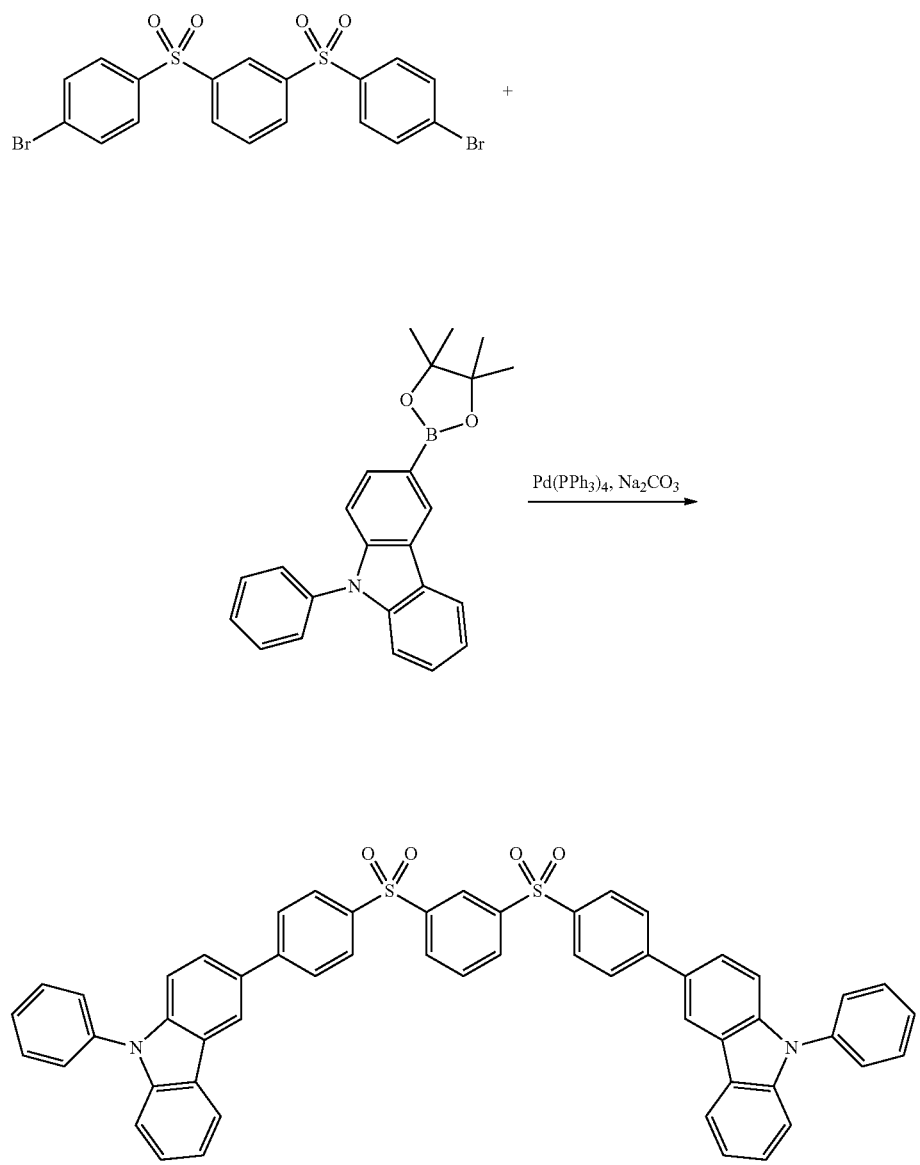

Under an argon atmosphere, adding 1,3-bis[(4-bromophenyl) sulfonyl]benzene (5 mmol, 2.6 g), 9-phenyl-3-(4,4,5,5-tetramethyl-1,3,2-dioxa pentaborane-2-yl)carbazole (12 mmol, 4.4 g), 30 ml toluene and 15 ml tetrahydrofuran to a reaction flask, then adding 30 ml sodium carbonate aqueous solution with a weight concentration of 10% and 50 mg tetrakis(triphenylphosphine)palladium, stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (2.2 g, the yield is 52%) is obtained.

Embodiment 15:

It is the preparation of a conjugated compound 1-5 containing a bis(phenylsulfonyl)benzene structure, and a reaction formula is shown as follows:

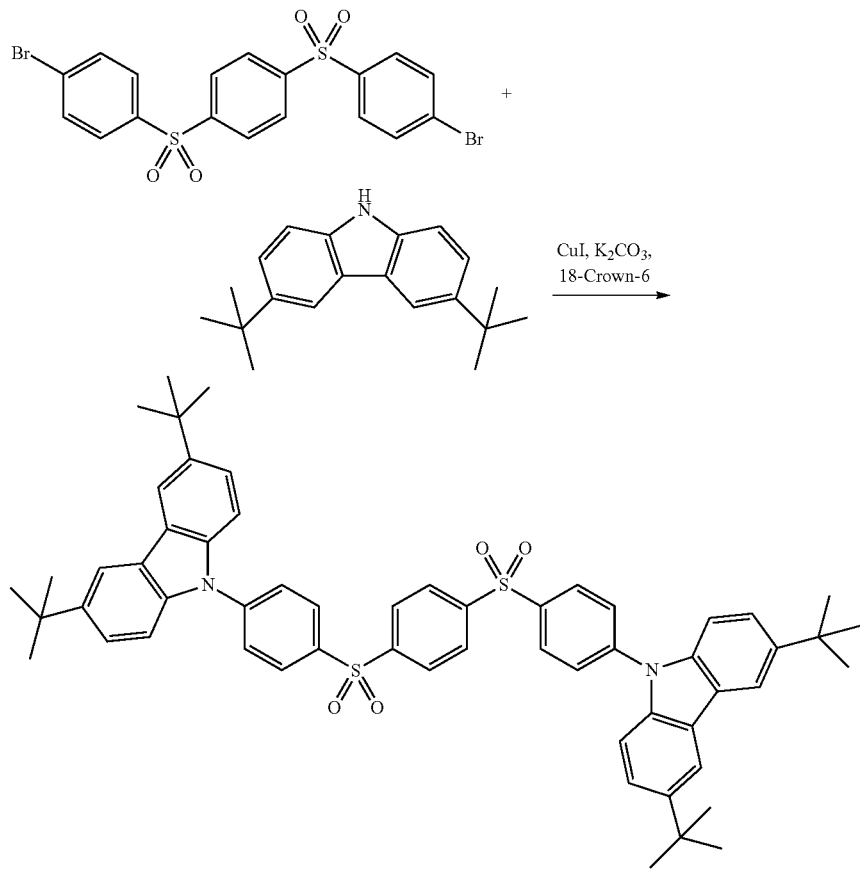

Under an argon atmosphere, adding 1,4-bis[(4-bromophenyl) sulfonyl]benzene (5 mmol, 2.6 g), 3,6-di-t-butyl-carbazole (11 mmol, 3.1 g), 20 ml 1,3-dimethyl-3,4,5,6-tetrahydro-2-pyrimidone used as solvent, 0.2 g cuprous iodide, 0.1 g 18-crown-6-ether, and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (2.4 g, the yield is 52%) is obtained.

Embodiment 16:

It is the preparation of a conjugated compound 2-5 containing a bis(phenylsulfonyl)benzene structure, and reaction formula is shown as follows:

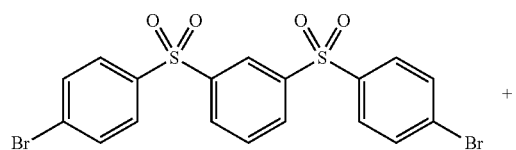

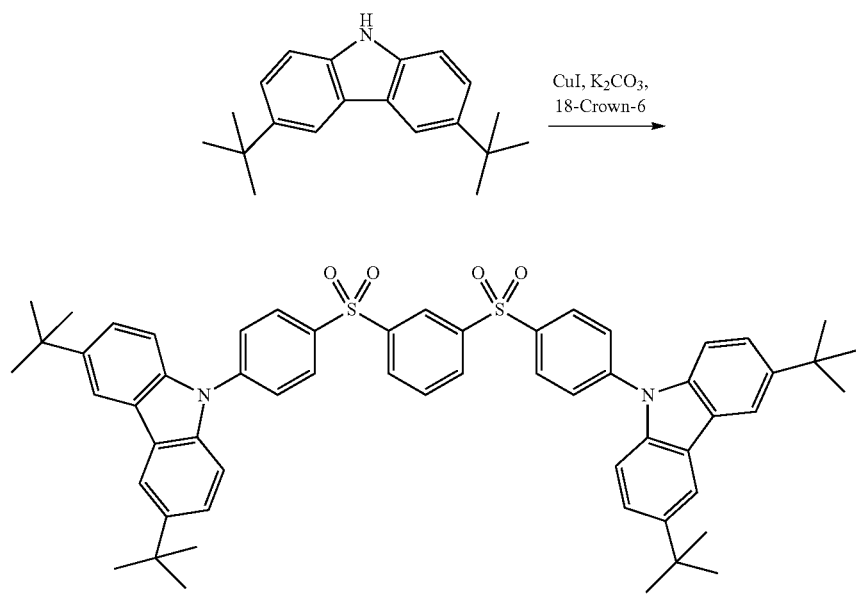

Under an argon atmosphere, adding 1,3-bis[(4-bromophenyl) sulfonyl]benzene (5 mmol, 2.6 g), 3,6-di-t-butyl-carbazole (11 mmol, 3.1 g), 20 ml 1,3-dimethyl-3,4,5,6-tetrahydro-2-pyrimidone used as solvent, 0.2 g cuprous iodide, 0.1 g 18-crown-6-ether, and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimation, a high purity product (2.7 g, the yield is 59%) is obtained.

Embodiment 17:

It is the preparation of a conjugated compound 1-6 containing a bis(phenylsulfonyl)benzene structure, and a reaction formula is shown as follows:

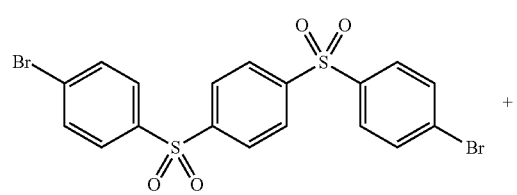

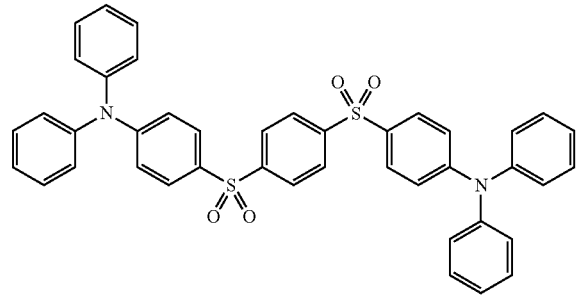

Under an argon atmosphere, adding 1,4-bis[(4-bromophenyl) sulfonyl]benzene (5 mmol, 2.6 g), diphenylamine (12 mmol, 2.0 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to obtain a pale yellow solid, and after drying and then vacuum sublimation, a high purity product (2.2 g, the yield is 63%) is obtained.

Embodiment 18:

It is the preparation of a conjugated compound 2-6 containing a bis(phenylsulfonyl)benzene structure, and a reaction formula is shown as follows:

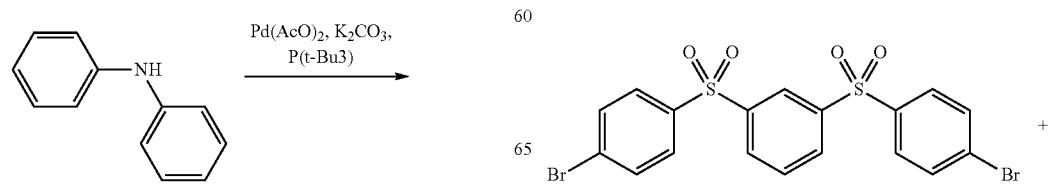

-continued

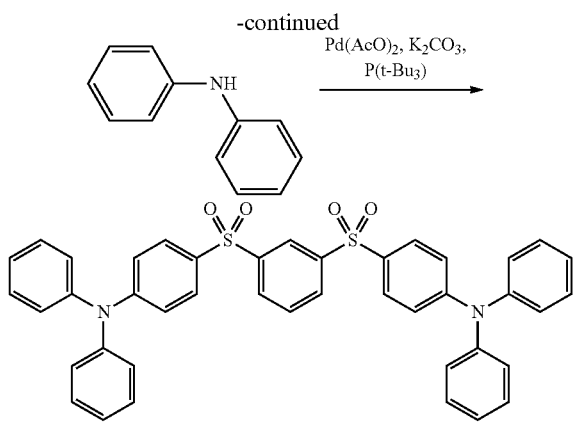

Under an argon atmosphere, adding 1,3-bis[(4-bromophenyl) sulfonyl]benzene (5 mmol, 2.6 g), diphenylamine (12 mmol, 2.0 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a pale yellow solid, and after drying and then vacuum sublimating, a high purity product (2.2 g, the yield is 63%) is obtained.

Embodiment 19:

It is the preparation of a conjugated compound 1-7 containing a bis(phenylsulfonyl)benzene structure, and a reaction formula is shown as follows:

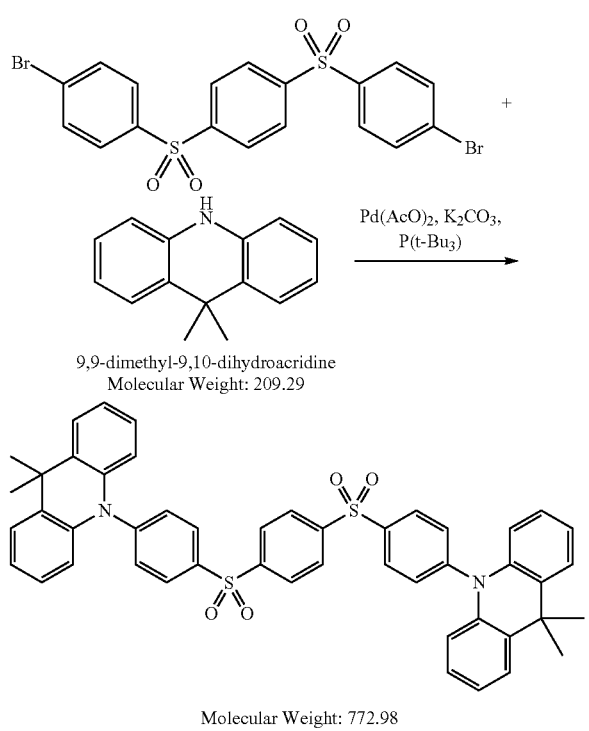

Under an argon atmosphere, adding 1,4-bis[(4-bromophenyl) sulfonyl]benzene (5 mmol, 2.6 g), 9,9-dimethyl-acridine (12 mmol, 2.5 g), 100 ml toluene used as a solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product with dichloromethane. Drying organic phases by anhydrous magnesium sulfate, removing solvent after separating, using silica gel column chromatography for separating and purifying to thereby obtain a white solid, and after drying and then vacuum sublimating, a high purity product (2.4 g, the yield is 62%) is obtained.

Embodiment 20:

It is the preparation of a conjugated compound 2-7 containing a bis(phenylsulfonyl) benzene structure, and a reaction formula is shown as follows:

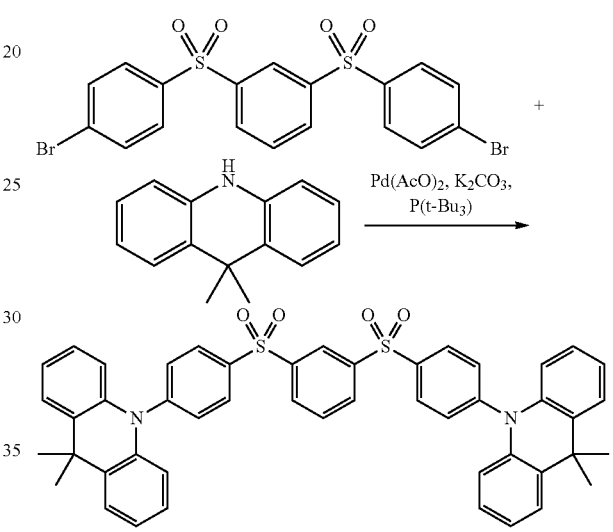

Under an argon atmosphere, adding 1,3-bis[(4-bromophenyl) sulfonyl]benzene (5 mmol, 2.6 g) and 9,9-dimethyl-acridine (12 mmol, 2.5 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a white solid, and after drying and then vacuum sublimating, a high purity product (2.2 g, the yield is 57%) is obtained.

Embodiment 21:

It is the preparation of a conjugated compound 1-8 containing a bis(phenylsulfonyl)benzene structure, and a reaction formula is shown as follows:

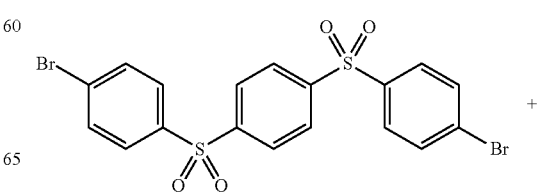

-continued

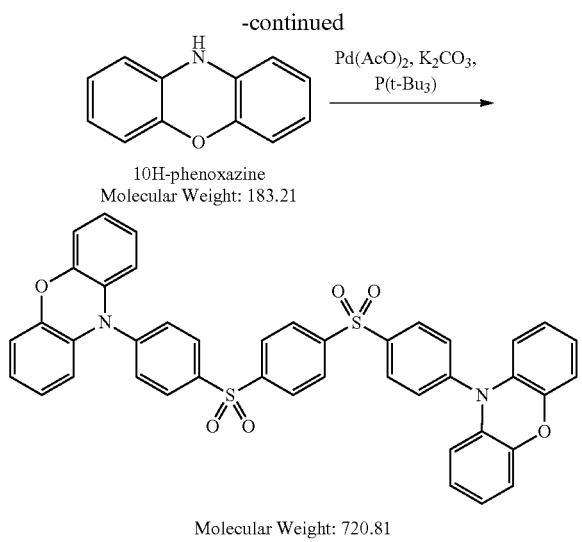

10H-phenoxazine
Molecular Weight: 183.21

Molecular Weight: 720.81

Under an argon atmosphere, adding 1,4-bis[(4-bromophenyl) sulfonyl]benzene (5 mmol, 2.6 g) and phenoxazine (12 mmol, 2.2 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a yellow solid, and after drying then vacuum sublimating, a high purity product (2.2 g, the yield is 61%) is obtained.

Embodiment 22:

It is the preparation of a conjugated compound 2-8 containing a bis(phenylsulfonyl)benzene structure, and a reaction formula is shown as follows:

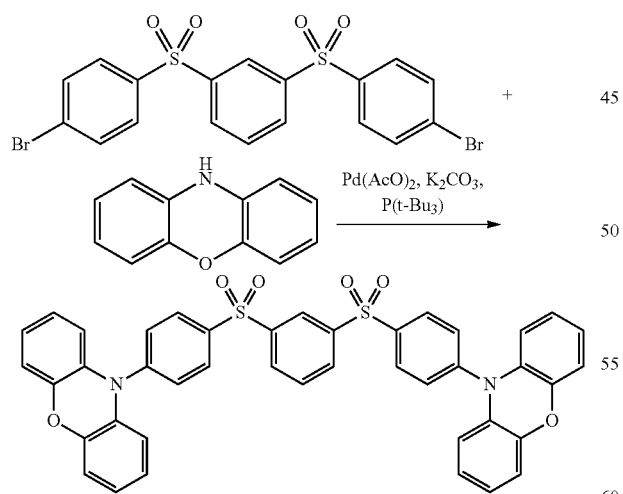

Under an argon atmosphere, adding 1,3-bis[(4-bromophenyl) sulfonyl]benzene (5 mmol, 2.6 g) and phenoxazine (12 mmol, 2.2 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a yellow solid, and after drying and then vacuum sublimating, a high purity product (2.0 g, the yield is 56%) is obtained.

Embodiment 23:

It is the preparation of a conjugated compound 1-9 containing a bis(phenylsulfonyl)benzene structure, and a reaction formula is shown as follows:

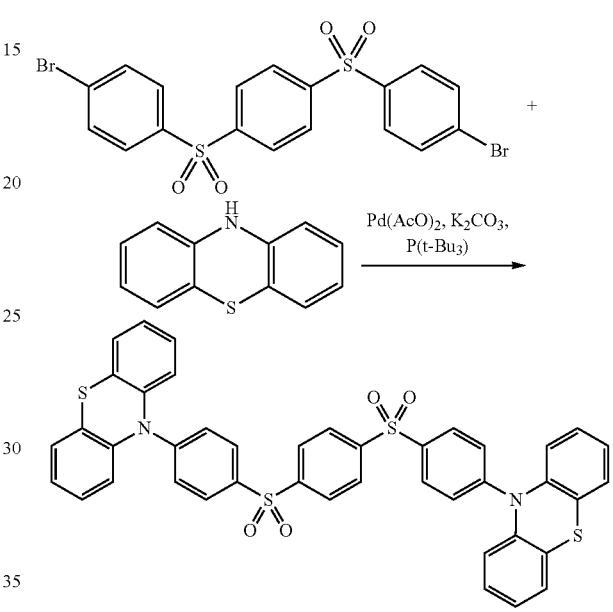

Under an argon atmosphere, adding 1,4-bis[(4-bromophenyl) sulfonyl]benzene (5 mmol, 2.6 g) and phenothiazine (12 mmol, 2.4 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a yellow solid, and after drying and then vacuum sublimating, a high purity product (2.4 g, the yield is 63%) is obtained.

Embodiment 24:

It is the preparation of a conjugated compound 2-9 containing a bis(phenylsulfonyl)benzene structure, and a reaction formula is shown as follows:

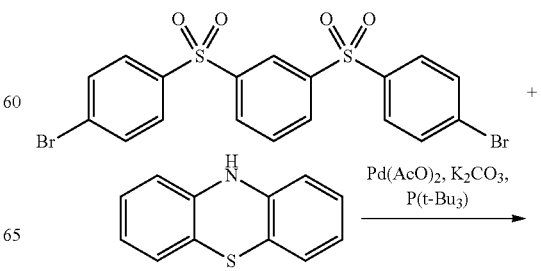

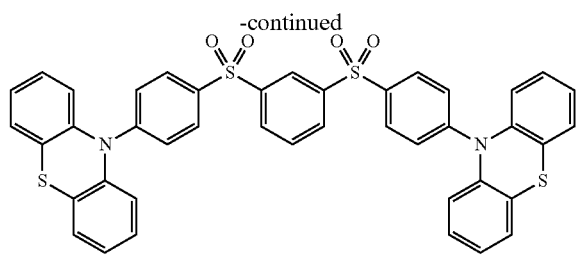

Under an argon atmosphere, adding 1,3-bis[(4-bromophenyl) sulfonyl]benzene (5 mmol, 2.6 g) and phenothiazine (12 mmol, 2.4 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a yellow solid, and after drying and then vacuum sublimating, a high purity product (2.2 g, the yield is 59%) is obtained.

Embodiment 25:

It is the preparation of a conjugated compound 1-10 containing a bis(phenylsulfonyl)benzene structure, and a reaction formula is shown as follows:

Under an argon atmosphere, adding 1,4-bis[(4-bromophenyl) sulfonyl]benzene (5 mmol, 2.6 g) and 5-benzene-9-hydrogen-phenazine (12 mmol, 3.1 g), 100 ml toluene used as solvent, 60 mg palladium acetate, tri-tert-butylphosphine (0.5 mmol, 0.11 g), and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a yellow solid, and after drying and then vacuum sublimating, a high purity product (2.4 g, the yield is 55%) is obtained.

Embodiment 26:

It is the preparation of a conjugated compound 2-10 containing a bis(phenylsulfonyl)benzene structure, and a reaction formula is shown as follows:

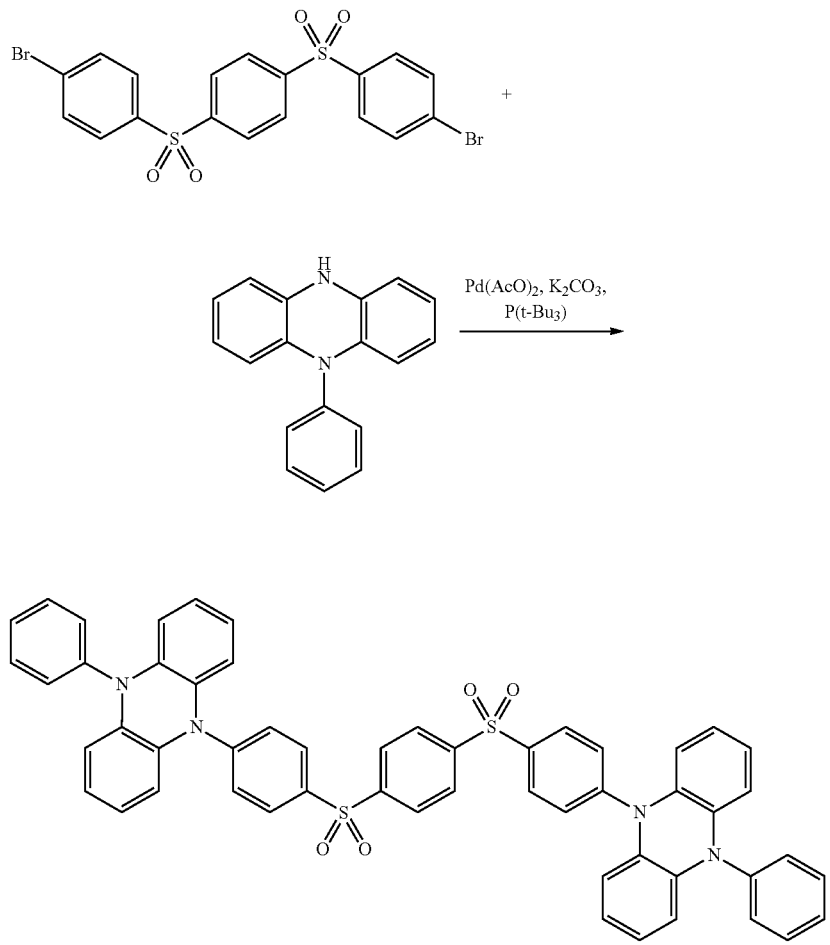

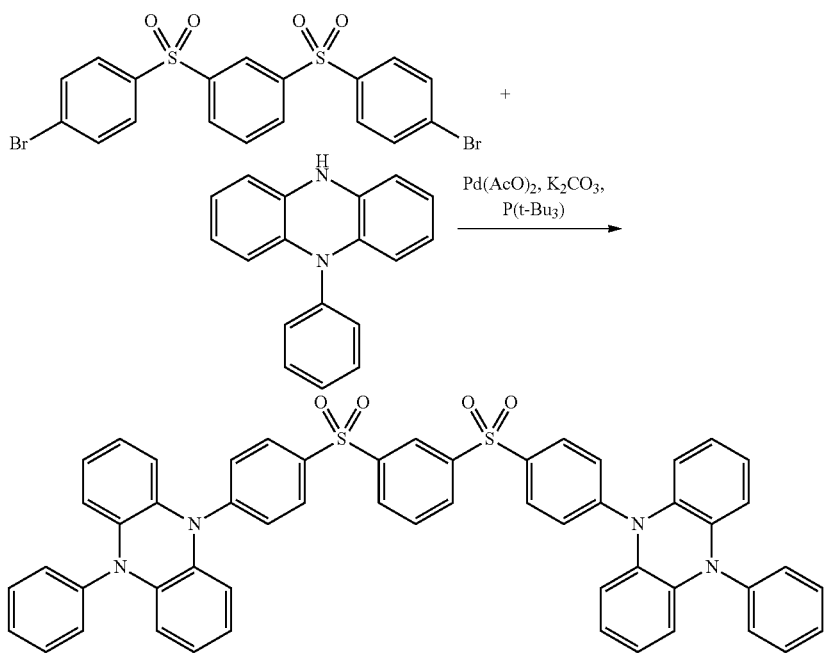

Under an argon atmosphere, adding 1,3-bis[(4-bromophenyl) sulfonyl]benzene (5 mmol, 2.6 g) and 5-benzene-9-hydrogen-phenazine (12 mmol, 3.1 g), 100 ml toluene used as solvent, 60 mg palladium acetate, tri-tert-butylphosphine (0.5 mmol, 0.11 g) and 1.5 g potassium carbonate to a reaction flask. Stirring to react for 24 h under heating reflux, cooling, then pouring the mixed liquor into 200 ml water, and extracting a product by dichloromethane. Drying organic phases by anhydrous magnesium sulfate, removing solvent after separating, using silica gel column chromatography for separating and purifying to thereby obtain a yellow solid, and after drying and then vacuum sublimating, a high purity product (2.3 g, the yield is 52%) is obtained.

The conjugated compounds 1-5, 2-5 containing a bis(phenylsulfonyl)benzene structure respectively obtained by the embodiment 15 and the embodiment 16 are used to fabricate organic light emitting diode (OLED) devices, and then are performed with performance testing:

The organic light-emitting diode devices each sequentially include, from bottom to top, a substrate, an anode, a hole transport layer, an electron blocking layer, a light-emitting layer, a hole blocking layer, an electron transport layer and a cathode. The substrate is a glass substrate, a material of the anode is indium tin oxide (ITO), the substrate and the anode together form an ITO glass, the ITO glass is processed with oxygen plasma after being cleaned with ultrasonic wave, a sheet resistance of the ITO glass is $10\Omega/cm^2$. A material of the hole transport layer is N,N'-diphenyl-N,N'-(1-naphthyl)-1,1'-biphenyl-4,4'-diamine (NPB), a material of the electron blocking layer is 4,4',4"-tris(9-carbazolyl)triphenylamine (TCTA), a material of the hole blocking layer is 9-4-tert-butylphenyl-3,6-di-triphenyl-silyl-9H-carbazole(CzSi), materials of the light-emitting layers each adopt a host material of bis(o-phenylene diphenyl phosphorus oxy)ether (DPEPO) doped with one of the conjugated compounds 1-5, 2-5 containing a bis(phenylsulfonyl)benzene structure which are obtained by the embodiment 15 and the embodiment 16, a material of the electron transport layer is 1,3,5-tris(1-phenyl-1-H-benzimidazol-2)benzene (TPBI); the cathode is a double-layer composite structure which is composed by a lithium fluoride (LiF) layer and an aluminum (Al) layer. A positive bias is applied between the anode and the cathode, characteristics of the devices are tested at different currents, and the results are shown in the table below.

TABLE 1

Performance list of the organic electroluminescent devices whose materials of light-emitting layer are the compounds 1-5, 2-5

| light-emitting layer | At the luminance of 1 cd/m² | | | | At the luminance of 100 cd/m² | | | |
|---|---|---|---|---|---|---|---|---|
| | V (V) | CE (cd/A) | PE (lm/W) | EQE (%) | V (V) | CE (cd/A) | PE (lm/W) | (%) |
| 1-5/DPEPO | 4.77 | 16.9 | 11.1 | 10.2 | 7.95 | 8.3 | 3.3 | 5.0 |
| 2-5/DPEPO | 5.11. | 3.7 | 2.3 | 4.6 | | | | |

Where, CE represents lumen efficiency, EQE represents external quantum efficiency, PE is power efficiency.

Figure 3:
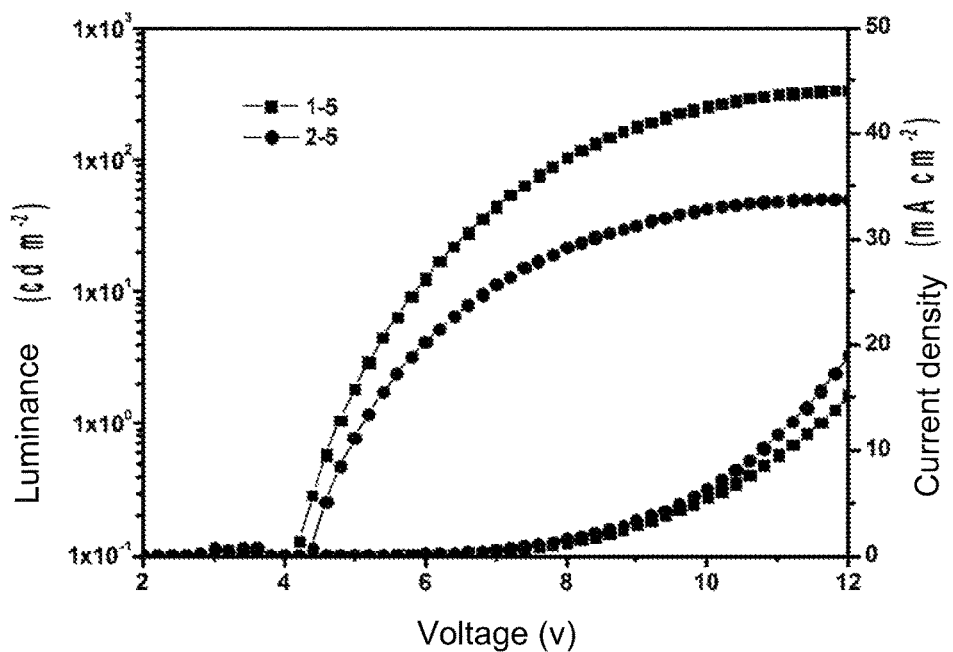
FIG. 3 is a voltage-current density-luminance relationship curve graph of organic light-emitting diode devices using the conjugated compounds containing a bis(phenylsulfonyl) benzene structures prepared by the embodiments 15, 16 of the invention as materials of light-emitting layer.
Figure 4:
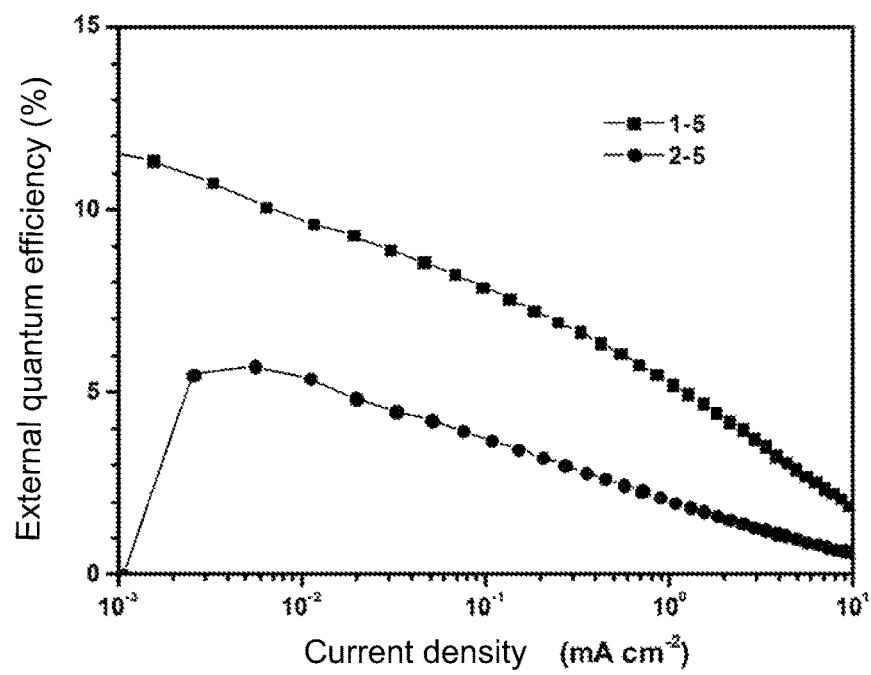
FIG. 4 is a current density-external quantum efficiency relationship curve graph of organic light emitting diode devices using the conjugated compounds containing a bis (phenylsulfonyl)benzene structure prepared by the embodiments 15, 16 of the invention as materials of light-emitting layer.
Figure 5:
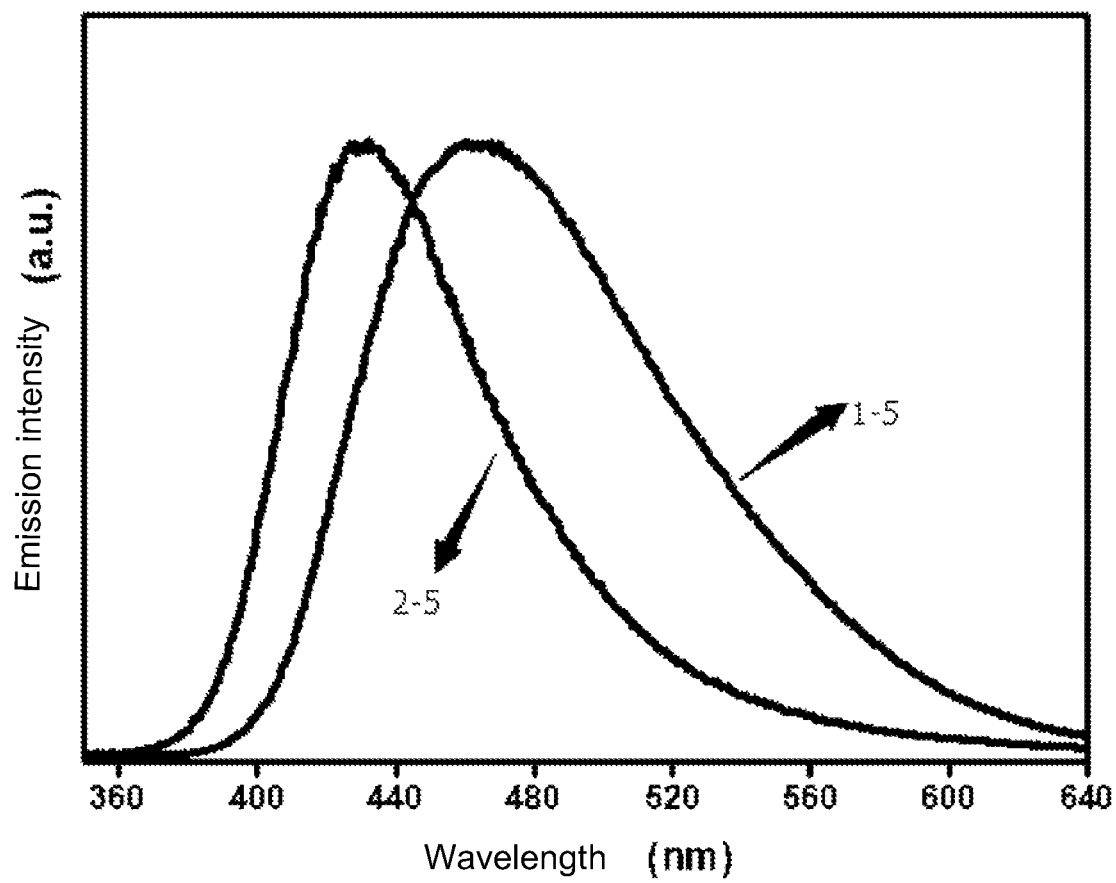
FIG. 5 is an electroluminescent spectra view of organic light emitting diode devices using the conjugated compounds containing a bis(phenylsulfonyl)benzene structure prepared by the embodiments 15, 16 of the invention as materials of light-emitting layer.

The voltage-current density-luminance relationship curve graph of the organic light-emitting diode devices using the conjugated compounds 1-5, 2-5 containing a bis(phenylsulfonyl)benzene structure prepared by embodiment 15, 16 as materials of light-emitting layer is illustrated in FIG. 3; theirs current density-external quantum efficiency relationship curve graph is illustrated in FIG. 4; theirs electroluminescent spectra view is illustrated in FIG. 5.

It can be seen from Table 1 and FIGS. 3-5, the conjugated compound containing a bis(phenylsulfonyl)benzene structure of the invention has a higher fluorescence quantum yield, the organic light-emitting diode device using such conjugated compound in its light-emitting layer can achieve a high luminous efficiency. Especially the OLED device based on the compound 1-5, its external quantum efficiency can reach to 10.2% at the luminance of 1 cd/m² and thus is far more than the theoretical limit of 5% in traditional fluorescent devices, it is shown that the conjugated compound containing a bis(phenylsulfonyl)benzene structure of the invention makes the excitons in the triplet state jump to the singlet state through an anti-interstitial, and then emit fluoresce by radiative transition, and as a result a high device luminous efficiency is achieved.

The conjugated compound containing a bis(phenylsulfonyl)benzene structure prepared by the invention, in addition to have a property of fluorescence and can be used to prepare the light-emitting layer, it also has a certain electrical conductivity, and thus can be applied to prepare the electron transport layer of organic electroluminescent diode.

The above embodiments are the most practical and preferred embodiments, but it can be understood that embodiments of the invention is not limited by the above embodiments, any other changes, modification, replacement, combination, simplification made not departing from the spirit and principles of the invention all are equivalent replacement means, and are all included within the scope of the invention.

What is claimed is:

1. A preparation method of a conjugated compound containing a bis(phenylsulfonyl)benzene structure, the conjugated compound comprising a chemical structure with one of structural general formulas as follows:

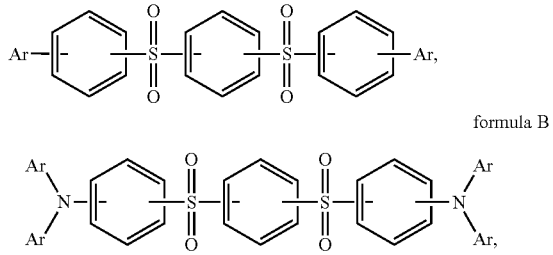

formula A formula B in the formula A and the formula B, each benzene ring being covalently bonded with adjacent sulfonyl group, Ar unit or N(Ar)₂ unit at an arbitrary position;
wherein the Ar unit has a conjugated structure and is one of aromatic rings constituted by vinylene group, ethynylene group and hydrogen and carbon atoms, aromatic heterocyclic rings constituted by carbon, nitrogen and hydrogen atoms, aromatic heterocyclic rings constituted by carbon, nitrogen, oxygen and hydrogen atoms, aromatic heterocyclic rings constituted by carbon, sulfur and hydrogen atoms, aromatic heterocyclic rings constituted by carbon, silicon and hydrogen atoms, aromatic heterocyclic rings constituted by carbon, nitrogen, sulfur and hydrogen atoms, aromatic heterocyclic rings constituted by carbon, silicon, sulfur and hydrogen atoms, and any combinations thereof;
the preparation method comprising following steps:
step 10, synthesizing a precursor of halogen-substituted bis(phenylsulfonyl)benzene;
step 20, making the synthesized precursor of halogen-substituted bis(phenylsulfonyl)benzene to react with a borate ester compound of a Ar unit in the presence of catalyst in a manner of Suzuki coupling reaction, to thereby prepare the conjugated compound containing a bis(phenylsulfonyl)benzene structure, and a reaction equation is as follows:

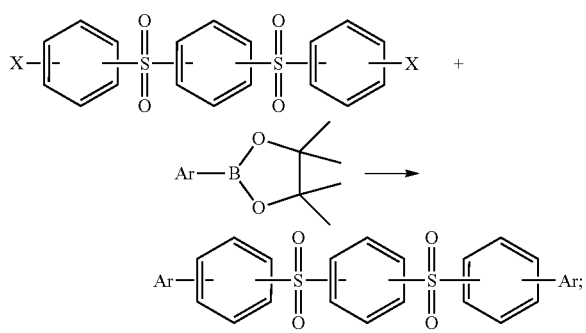

or,
step 20', making the synthesized precursor of halogen-substituted bis(phenylsulfonyl)benzene to react with a NH(Ar)₂ compound containing secondary amine atoms in a manner of Buchwald-Hartwig coupling reaction or copper-catalyzed halogenated aromatic amination reaction to thereby prepare the conjugated compound containing a bis(phenylsulfonyl)benzene structure, and a reaction equation is as follows:

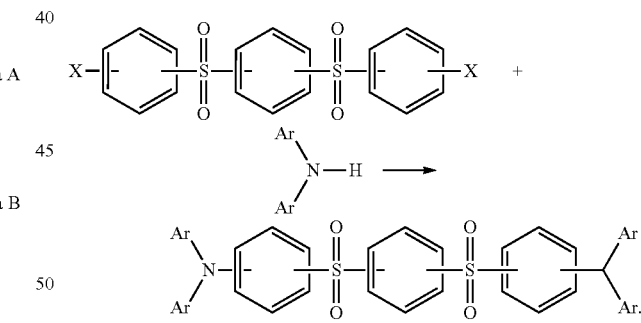

2. The preparation method of a conjugated compound containing a bis(phenylsulfonyl)benzene structure as claimed in claim 1, wherein the step 10 concretely comprises following steps:
step 11, dissolving a halogenated thiophenol and a dichloro-dicyano-p-benzoquinone (DDQ) in a solvent, heating to react, and thereby obtaining a halogenated diphenyl disulfide;
step 12, dissolving the halogenated diphenyl disulfide, a dihalogeno-benzene, a catalyst and an alkali in a solvent, heating to react and thereby obtaining a halogen-substituted bis(phenylsulfenyl)benzene;
step 13, dissolving the halogen-substituted bis(phenylsulfenyl)benzene in a solvent, adding an oxidizer, heating to react and thereby obtaining the halogen-substituted bis(phenylsulfonyl)benzene.

3. The preparation method of a conjugated compound containing a bis(phenylsulfonyl)benzene structure as claimed in claim 2, wherein the step 20 concretely is that dissolving the synthesized halogen-substituted bis(phenylsulfonyl)benzene, the borate ester of the Ar unit, the catalyst and the alkali in a solvent, heating to react and thereby obtaining the conjugated compound containing a bis(phenylsulfonyl)benzene structure;

the step 20' concretely is that dissolving the synthesized halogen-substituted bis(phenylsulfonyl)benzene, the NH(Ar)$_2$ compound containing secondary amine atoms, the catalyst and the alkali in a solvent, heating to react and thereby obtaining the conjugated compound containing a bis(phenylsulfonyl)benzene structure.

4. The preparation method of a conjugated compound containing a bis(phenylsulfonyl)benzene structure as claimed in claim 3, wherein:

in the step 11, a molar ratio of the halogenated thiophenol to the dichloro-dicyano-p-benzoquinone is 2:1;

in the step 12, a molar ratio of the halogenated diphenyl disulfide, the dihalogeno-benzene, the catalyst and the alkali is (1~1.2):1:(0.02~0.05):(2~6);

in the step 13, a molar ratio of the halogen-substituted bis(phenylsulfenyl)benzene to the oxidizer is 1:(5~8);

in the step 20, a molar ratio of the halogen-substituted bis(phenylsulfonyl)benzene, the borate ester of the Ar unit, the catalyst and the alkali is 1:(2.2~3): (0.02~0.05):(3~6);

in the step 20', a molar ratio of the halogen-substituted bis(phenylsulfonyl)benzene, the NH(Ar)$_2$ compound containing secondary amine atoms, the catalyst and the alkali is 1: (2.2~3):(0.05~0.1):(3~6).

5. The preparation method of a conjugated compound containing a bis(phenylsulfonyl)benzene structure as claimed in claim 3, wherein:

in the step 11, the halogenated thiophenol is at least one of ortho-bromobenzenethiol, para-bromobenzenethiol and meta-bromobenzenethiol;

in the step 12, the dihalogeno-benzene is at least one of para-diiodobiphenyl and meta-diiodobiphenyl, the catalyst is at least one of cuprous sulfide, cuprous iodide and cuprous oxide;

in the step 13, the oxidizer is at least one of hydrogen peroxide, potassium permanganate and pyridinium chlorochromate;

in the step 20, the catalyst is at least one of tetrakis (triphenylphosphine)palladium, tetrakis(triphenylphosphine)palladium dichloride, tris(dibenzylideneacetone) dipalladium and phosphorus tricyclohexylphosphine;

in the step 20', the catalyst is one of palladium acetate, tri-butyl phosphine and 1,1'-bis(diphenylphosphino) ferrocene;

in the steps 12, 20 and 20', the alkalis are at least one of potassium carbonate, sodium carbonate and potassium phosphate;

in the steps 11, 12, 13, 20 and 20', the solvents are at least one of toluene, ethanol, 1,4-dioxane, tetrahydrofuran, dimethyl sulfoxide, methylene chloride, N, N-dimethylformamide and 1,3-dimethyl-3,4,5,6-tetrahydro-2-pyrimidone.

6. An organic electroluminescent diode device, comprising a substrate, an anode, a hole transport layer, an electron blocking layer, a light-emitting layer, a hole blocking layer, an electron transport layer and a cathode sequentially arranged in that order from bottom to top, wherein a material of the light-emitting layer is a host material doped with a conjugated compound containing a bis(phenylsulfonyl)benzene structure, the host material is bis(o-phenylene diphenyl phosphorus oxy)ether;

wherein the conjugated compound containing a bis(phenylsulfonyl)benzene structure comprises a chemical structure with one of structural general formulas as follows:

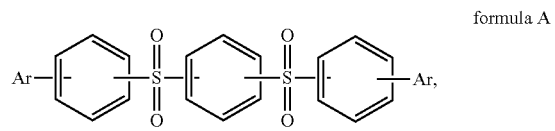

formula A

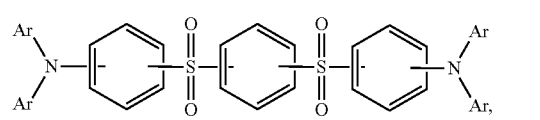

formula B in the formula A and the formula B, each benzene ring being covalently bonded with adjacent sulfonyl group, Ar unit or N(Ar)$_2$ unit at an arbitrary position;

wherein the Ar unit has a conjugated structure and is one of aromatic rings constituted by vinylene group, ethynylene group and hydrogen and carbon atoms, aromatic heterocyclic rings constituted by carbon, nitrogen and hydrogen atoms, aromatic heterocyclic rings constituted by carbon, nitrogen, oxygen and hydrogen atoms, aromatic heterocyclic rings constituted by carbon, sulfur and hydrogen atoms, aromatic heterocyclic rings constituted by carbon, silicon and hydrogen atoms, aromatic heterocyclic rings constituted by carbon, nitrogen, sulfur and hydrogen atoms, aromatic heterocyclic rings constituted by carbon, silicon, sulfur and hydrogen atoms, and any combinations thereof.

7. The organic electroluminescent diode device as claimed in claim 6, wherein the substrate is a glass substrate, a material of the anode is indium tin oxide, the cathode is a double-layer composite structure which is composed by a lithium fluoride layer and an aluminum layer.

8. The organic electroluminescent diode device as claimed in claim 6, wherein a material of the hole transport layer is N,N'-diphenyl-N,N'-(1-naphthyl)-1,1'-biphenyl-4,4'-diamine, a material of the electron blocking layer is 4,4',4"-tris(9-carbazolyl)triphenylamine, a material of the hole blocking layer is 9-4-tert-butylphenyl-3,6-di-triphenylsilyl-9H-carbazole, a material of the electron transport layer is 1,3,5-tris(1-phenyl-1-H-benzimidazol-2-pyrimidone)benzene.

9. The preparation method of a conjugated compound containing a bis(phenylsulfonyl)benzene structure as claimed in claim 1, wherein the middle benzene ring of the conjugated compound is covalently bonded with the adjacent sulfonyl group in the form of meta-position or para-position, the benzene rings at both sides of the sulfonyl group each are covalently bonded with the adjacent Ar unit or N(Ar)$_2$ unit in the form of para-position, and thereby the conjugated compound containing a bis(phenylsulfonyl)benzene structure has a chemical structure with one of structural general formulas as follows:

conjugated compound containing a bis(phenylsulfonyl)benzene structure has a chemical structure with one of structural general formulas as follows:

formula C
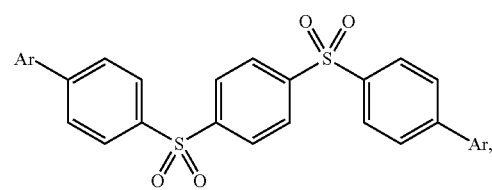

formula D
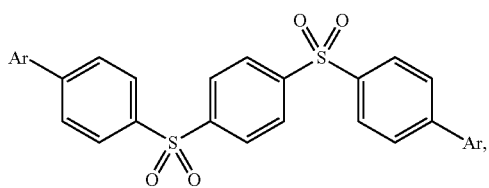

formula E
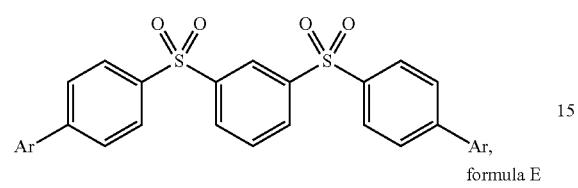

formula F
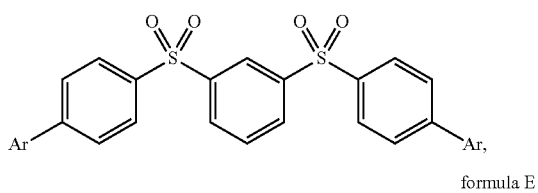

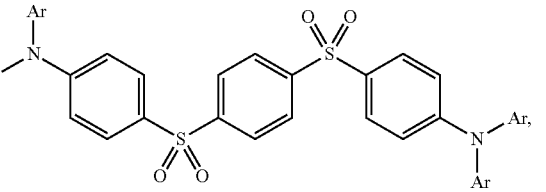

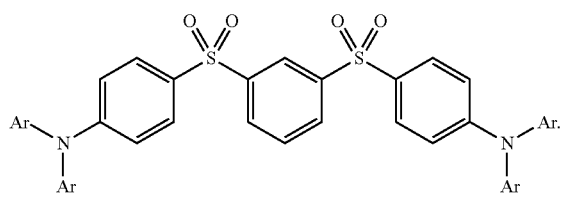

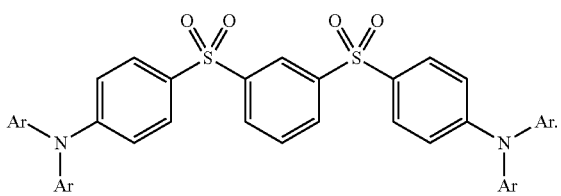

10. The organic electroluminescent diode device as claimed in claim 6, wherein the middle benzene ring of the conjugated compound is covalently bonded with the adjacent sulfonyl group in the form of meta-position or para-position, the benzene rings at both sides of the sulfonyl group each are covalently bonded with the adjacent Ar unit or $N(Ar)_2$ unit in the form of para-position, and thereby the

* * * * *